United States Patent
Hoem et al.

(10) Patent No.: US 10,105,376 B2
(45) Date of Patent: Oct. 23, 2018

(54) OMEGA-3 COMPOSITIONS

(71) Applicant: AKER BIOMARINE ANTARCTIC AS, Stamsund (NO)

(72) Inventors: Nils Hoem, Oslo (NO); Lena Burri, Oslo (NO); Kjetil Berge, Oslo (NO)

(73) Assignee: AKER BIOMARINE ANTARCTIC AS, Stamsund (NO)

( * ) Notice: Subject to any disclaimer, the term of this patent is extended or adjusted under 35 U.S.C. 154(b) by 58 days.

(21) Appl. No.: 14/035,167

(22) Filed: Sep. 24, 2013

(65) Prior Publication Data

US 2014/0088043 A1   Mar. 27, 2014

Related U.S. Application Data

(60) Provisional application No. 61/775,032, filed on Mar. 8, 2013, provisional application No. 61/739,260, filed on Dec. 19, 2012, provisional application No. 61/704,854, filed on Sep. 24, 2012.

(51) Int. Cl.
*A61K 31/685* (2006.01)
*A61K 9/48* (2006.01)
*A61K 31/66* (2006.01)

(52) U.S. Cl.
CPC .......... *A61K 31/685* (2013.01); *A61K 9/4858* (2013.01)

(58) Field of Classification Search
CPC ......... A61K 31/685; A61K 31/66; A61K 9/48
USPC ........................................ 514/78, 114, 121
See application file for complete search history.

(56) References Cited

U.S. PATENT DOCUMENTS

| | | | |
|---|---|---|---|
| 5,656,667 A | 8/1997 | Breivik | |
| 2008/0274203 A1* | 11/2008 | Bruheim | A61K 9/4858 424/522 |
| 2011/0223246 A1 | 9/2011 | Opheim | |

FOREIGN PATENT DOCUMENTS

| | | | | |
|---|---|---|---|---|
| WO | WO 0048592 A1 * | 8/2000 | ............. | A61K 31/23 |
| WO | WO-0048592 A1 * | 8/2000 | ............. | A61K 31/23 |
| WO | 2006/054183 | 5/2006 | | |
| WO | 2008/060163 | 5/2008 | | |
| WO | 2008/117062 | 10/2008 | | |
| WO | 2009/139641 | 11/2009 | | |

OTHER PUBLICATIONS

Steffers, W. et al., Aquaculture, vol. 151 pp. 97-119, published 1997.*
W. Steffens (Aquaculture vol. 151, pp. 97-119, published 1997).*
Fatty Acid Composition of Fish Oils: United States Departmetn of the Interior Fish and Wildlife Service Bureau of Commercial Fisheries. Published 1965. (Year: 1965).*
Grupp, et al., J. Mol. Cell. Cardio. 31: 297-303 (1999).

* cited by examiner

*Primary Examiner* — Timothy P Thomas
*Assistant Examiner* — George W Kosturko
(74) *Attorney, Agent, or Firm* — Casimir Jones S.C.; J. Mitchell Jones

(57) ABSTRACT

The present invention relates to compositions comprising omega-3 fatty acid derivatives, and in particular to compositions comprising omega-3 phospholipids in combination with other omega-3 derivatives.

6 Claims, No Drawings

OMEGA-3 COMPOSITIONS

CROSS-REFERENCE TO RELATED APPLICATIONS

This application claims priority to U.S. Provisional Patent Application No. 61/704,854, filed Sep. 24, 2012, and to U.S. Provisional Patent Application No. 61/739,260, filed Dec. 19, 2012, and to U.S. Provisional Patent Application No. 61/775,032, filed Mar. 8, 2013, the contents of which are incorporated by reference in their entireties.

FIELD OF THE INVENTION

The present invention relates to compositions comprising omega-3 fatty acid derivatives, and in particular to compositions comprising omega-3 phospholipids in combination with other omega-3 derivatives.

BACKGROUND OF THE INVENTION

Accumulating evidence indicates that long chain omega-3 fatty acids found in fish, docosahexaenoic acid (DHA) and eicosapentaenoic acid (EPA), decrease the risk of CHD and ischemic heart disease. Large epidemiological studies, such as the Physicians' Health Study and the Nurses' Health Study, examined dietary and other lifestyle factors that influence health outcomes. The Physician's Health Study reported that consumption of one or more servings of fish per week was associated with a 52% lower risk of sudden cardiac disease compared to less than one fish meal per week. In another epidemiological study, the Nurses Health Study in America, it was found that consumption of five or more servings of fish per week was associated with 45% fewer cardiac deaths compared to consumption of one fish meal per month. Long chain omega-3 fatty acids are known to be a protective dietary factor for cardiovascular disease. EPA and DHA have been shown to lower triglyceride levels and act as anti-arrhythmic agents. The American Heart Association (AHA) performed comprehensive reviews of the data for fish and fish oil consumption and cardiovascular disease. The AHA report recommends that individuals with and without heart disease and elevated blood triglyceride levels consume fish or take a fish oil supplement. A report prepared in 2003 by The Third Task Force of European and Other Societies also recommends fish oil as a standard therapy for post-myocardial infarction management.

The level of triglycerides in blood is positively associated with an increase in CHD, as triglyceride levels increase so does the risk of CHD. Multiple factors influence the elevation of serum triglycerides throughout life with a major contributor being the diet. Both DHA and EPA, which are abundant in many marine seafood products, appear to support cardiovascular health and lower blood triglyceride levels. It is known that fish oil can reduce serum triglyceride levels by 20-50%, similar to the effects observed with medications such as statins, niacin and fibrates. The American Heart Association recommends that individuals without documented CHD consume two servings of fish (preferably fatty fish, please see Food products) per week. Patients with CHD should consume 1 gram of EPA and DHA per day preferably from fatty fish or in a supplemental form (if under the care of a physician). For those patients who need to lower triglyceride levels, the American Heart Association recommends 2-4 grams of EPA and DHA per day in supplemental form under a physician's care. A prescription form of EPA and DHA, Lovaza (formerly known as Omacor), is a good omega-3 fatty acid source available for people with high levels of blood triglycerides. Each Lovaza 1 gram capsule contains 465 mg EPA ethyl ester, 375 mg DHA ethyl ester, 80 mg of other omega-3 fatty acids, 30 mg of omega-6 fatty acids and 50 mg of antioxidants. It is prescribed as an adjunct to diet to reduce very high triglyceride levels in adult patients.

In medical research, omega-3 fatty acids are being investigated to determine whether they can effectively improve a wide range of disease states-among them, heart disease, diabetes, inflammation, depression, Alzheimer's and attention deficit disorder—making this group of nutrients an exciting and very active area of clinical research. Ensuring that omega-3 fatty acids are a part of the diet as recommended by dietary guidelines is a proper starting point to achieving better health; hence, a great opportunity exists in the potential for improving the human condition with omega-3 fatty acids.

Oral administration of omega-3 compositions to some subjects results in unwanted side effects, including burping and reflux. The biological availability of some forms of omega-3 may also be limited. Accordingly, what is needed in the art are improved omega-3 formulations.

SUMMARY OF THE INVENTION

The present invention relates to compositions comprising omega-3 fatty acid derivatives, and in particular to compositions comprising omega-3 phospholipids in combination with other omega-3 derivatives.

In some embodiments, the present invention provides compositions comprising a mixture of phospholipid compounds having the following structure:

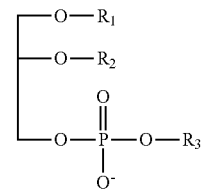

wherein R1 and R2 are selected from the group consisting of a fatty acid moiety and H and R3 is H or a choline, ethanolamine, inositol and serine moiety, said mixture of phospholipid compounds comprising more than about 90% choline moieties at position R3 and more than about 20% w/w omega-3 fatty acid moieties, wherein more than about 90% w/w of said omega-3 fatty acid moieties are at position R2, and a mixture of omega-3 fatty acid derivatives selected from the group consisting of:

a mixture of glyceride compounds having the following structure:

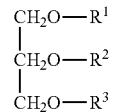

wherein at least one of either R1, R2, and R3 is a an omega-3 fatty acid moiety, and the other two of either R1, R2 and R3 may H or a fatty acid moiety, and esters and free fatty acids of omega-3 fatty acids, and combinations thereof.

In some embodiments, the mixture of omega-3 fatty acid derivatives comprises at least 20% omega-3 fatty acid moieties on a w/w basis. In some embodiments, the mixture of omega-3 fatty acid derivatives comprises at least 20% omega-3 fatty acid moieties on a w/w basis. In some embodiments, the mixture of omega-3 fatty acid derivatives comprises at least 50% omega-3 fatty acid moieties on a w/w basis. In some embodiments, the mixture of omega-3 fatty acid derivatives comprises at least 65% omega-3 fatty acid moieties on a w/w basis. In some embodiments, the composition comprises at least 80% omega-3 fatty acid moieties on a w/w basis. In some embodiments, the omega-3 fatty acid moieties are selected from the group consisting of eicosapentaenoic acid, docosahexaenoic acid, and combinations thereof. In some embodiments, the composition comprises at least 5% w/w of said phospholipid compounds. In some embodiments, the composition comprises at least 25% w/w of said phospholipid compounds. In some embodiments, the composition comprises at least 50% w/w of said phospholipid compounds. In some embodiments, the composition comprises at least 70% w/w of said phospholipid compounds. In some embodiments, the omega-3 moieties in said mixture of phospholipid compounds are eicosapentaenoic acid and said docosahexaenoic acid and wherein said eicosapentaenoic acid and said docosahexaenoic acid are present in a ratio of eicosapentaenoic acid:docosahexaenoic acid of from about 1:1 to about 3:1.

In some embodiments, the composition comprises at least 10% ethyl esters comprising said omega-3 fatty acid moieties. In some embodiments, the composition comprises at least 10% ethyl esters comprising said omega-3 fatty acid moieties. In some embodiments, the composition comprises at least 30% ethyl esters comprising said omega-3 fatty acid moieties. In some embodiments, the composition comprises at least 50% ethyl esters comprising said omega-3 fatty acid moieties. In some embodiments, the composition comprises at least 70% ethyl esters comprising said omega-3 fatty acid moieties. In some embodiments, the composition comprises at least 90% ethyl esters comprising said omega-3 fatty acid moieties.

In some embodiments, the composition comprises at least 10% glyceride compounds comprising said omega-3 fatty acid moieties. In some embodiments, the composition comprises at least 30% glyceride compounds comprising said omega-3 fatty acid moieties. In some embodiments, the composition comprises at least 50% glyceride compounds comprising said omega-3 fatty acid moieties. In some embodiments, the composition comprises at least 70% glyceride compounds comprising said omega-3 fatty acid moieties. In some embodiments, the composition comprises at least 90% glyceride compounds comprising said omega-3 fatty acid moieties.

In some embodiments, the composition comprises at least 10% omega-3 free fatty acids. In some embodiments, the composition comprises at least 30% omega-3 free fatty acids. In some embodiments, the composition comprises at least 50% omega-3 free fatty acids. In some embodiments, the composition comprises at least 70% omega-3 free fatty acids. In some embodiments, the composition comprises at least 90% omega-3 free fatty acids.

In some embodiments, the omega-3 fatty acid moieties or free fatty acids are selected from the group consisting of eicosapentaenoic acid and docosahexaenoic acid and combinations thereof. In some embodiments, the eicosapentaenoic acid and said docosahexaenoic acid are present in a ratio of eicosapentaenoic acid:docosahexaenoic acid of from about 1:1 to about 3:1. In some embodiments, the composition comprises astaxanthin. In some embodiments, the comprises at least a second antioxidant. In some embodiments, the composition is partially or totally derived from krill. In some embodiments, the composition is provided in a formulation selected from the group consisting of a capsule, a tablet, a liquid, a powder, an emulsion, a dietary supplement, a nutritional supplement, a beverage and a functional food.

In some embodiments, the present invention provides for oral or intravenous administration of the foregoing compositions to a subject to reduce serum triglycerides, reduce serum cholesterol, reduce plaque formation, reduce platelet aggregation, treat atherosclerosis, improve cardiovascular health, reduce inflammation, reduce coronary heart disease, treat depression, treat Alzheimer's disease, treat attention deficit disorder, and treat metabolic syndrome. In some embodiments, the composition is administered in a daily dose of from about 0.1 to about 3 grams. In some embodiments, the composition is administered to a subject selected from the group consisting of humans, non-human primates, domestic raised or farmed animals, and companion animals.

Definitions

As used herein, "phospholipid" refers to an organic compound having the following general structure:

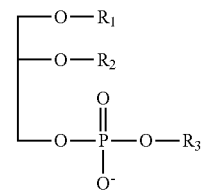

wherein R1 is a fatty acid residue or —H, R2 is a fatty acid residue or —H, and R3 is a —H or a phospholipid headgroup moiety such as a choline ($HOCH_2CH_2N^+$ $(CH_3)_3OH^-$) moiety, ethanolamine ($HOCH_2CH_2NH_2$) moiety, serine moiety, inositol moiety such as cyclohexane polyol inositol, and derivatives thereof. Preferably, R1 and R2 cannot simultaneously be —H. When R3 is an —H, the compound is a diacylglycerophosphate, while when R3 is a nitrogen-containing compound, the compound is a phosphatide such as lecithin, cephalin, phosphatidyl serine or plasmalogen.

An "ether phospholipid" as used herein refers to a phospholipid having an ether bond at position 1 the glycerol backbone. Examples of ether phospholipids include, but are not limited to, alkylacylphosphatidylcholine (AAPC), lyso-alkylacylphosphatidylcholine (LAAPC), and alkylacylphosphatidylethanolamine (AAPE). A "non-ether phospholipid" is a phospholipid that does not have an ether bond at position 1 of the glycerol backbone.

As used herein, the term "long chain polyunsaturated fatty acid" refers to a fatty acid having 20 or more carbons and which is unsaturated at two or more bonds.

As used herein, the term omega-3 fatty acid refers to polyunsaturated fatty acids that have the final double bond in the hydrocarbon chain between the third and fourth carbon atoms from the methyl end of the molecule. Non-limiting examples of omega-3 fatty acids include, 5,8,11, 14,17-eicosapentaenoic acid (EPA), 4,7,10,13,16,19-docosahexanoic acid (DHA) and 7,10,13,16,19-docosapentanoic acid (DPA).

As used herein, the term "moiety" when used in reference to a fatty acid refers to the portion of the fatty acid bound to another molecule via a bond, such as an ester or ether linkage to for example, a glyceride or phosphoglyceride molecule.

As used herein, the term "physiologically acceptable carrier" refers to any carrier or excipient commonly used with oily pharmaceuticals. Such carriers or excipients include, but are not limited to, oils, starch, sucrose and lactose.

As used herein, the term "oral delivery vehicle" refers to any means of delivering a pharmaceutical orally, including, but not limited to, capsules, pills, tablets and syrups.

As used herein, the term "food product" refers to any food or feed suitable for consumption by humans, non-ruminant animals, or ruminant animals. The "food product" may be a prepared and packaged food (e.g., mayonnaise, salad dressing, bread, or cheese food) or an animal feed (e.g., extruded and pelleted animal feed or coarse mixed feed). "Prepared food product" means any pre-packaged food approved for human consumption.

As used herein, the term "foodstuff" refers to any substance fit for human or animal consumption.

As used herein, the term "functional food" refers to a food product to which a biologically active supplement has been added.

As used herein, the term "infant food" refers to a food product formulated for an infant such as formula.

As used herein, the term "elderly food" refers to a food product formulated for persons of advanced age.

As used herein, the term "pregnancy food" refers to a food product formulated for pregnant women.

As used herein, the term "nutritional supplement" refers to a food product formulated as a dietary or nutritional supplement to be used as part of a diet.

DETAILED DESCRIPTION OF THE INVENTION

The present invention relates to compositions comprising omega-3 fatty acid derivatives, and in particular to compositions comprising omega-3 phospholipids in combination with other omega-3 derivatives. The improved omega-3 formulations of the present invention exhibit increased bioavailability as well as decreased adverse reaction in users such as decreased burping and reflux.

In some embodiments, the omega-3 derivative is a phospholipid compound. In some embodiments, the present invention provides compositions comprising a mixture of phospholipid compounds having the following structure:

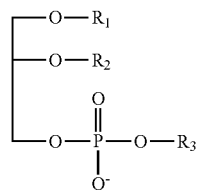

wherein R1 and R2 are selected from the group consisting of a fatty acid moiety and H and R3 is H or a choline, ethanolamine, inositol and serine moiety, said mixture of phospholipid compounds comprising more than about 90% choline moieties at position R3 and more than about 30% w/w omega-3 fatty acid moieties at R1 and R2, and wherein more than about 90% w/w of said omega-3 fatty acid moieties are at position R2.

In some embodiments, the omega-3 fatty acid moiety selected from the group consisting of Eicosatrienoic acid (ETE; 20:3 (n-3); all-cis-11,14,17-eicosatrienoic acid); Eicosatetraenoic acid (ETA; 20:4 (n-3); all-cis-8,11,14,17-eicosatetraenoic acid); Eicosapentaenoic acid (EPA; 20:5 (n-3); all-cis-5,8,11,14,17-eicosapentaenoic acid); Heneicosapentaenoic acid (HPA; 21:5 (n-3); all-cis-6,9,12,15,18-heneicosapentaenoic acid); Docosapentaenoic acid (DPA; 22:5 (n-3); all-cis-7,10,13,16,19-docosapentaenoic acid; Docosahexaenoic acid (DHA; 22:6 (n-3); all-cis-4,7,10,13,16,19-docosahexaenoic acid); Tetracosapentaenoic acid (24:5 (n-3); all-cis-9,12,15,18,21-tetracosapentaenoic acid; and Tetracosahexaenoic acid (24:6 (n-3) all-cis-6,9,12,15,18,21-tetracosahexaenoic acid). In some embodiments, the omega-3 fatty acid moiety is bound through an ester bond at the R1 or R2 position (to provide an acylphospholipid), while in other embodiments, the LC-PUFA moiety is bound through an ether bond or vinyl ether bond (to provide an ether phospholipid, alkylacylphospholipid, or alkenylacylphospholipid).

In embodiments where at least one of R1 and R2 is an omega-3 fatty acid moiety, the other of R1 and R2 may be any organic moiety which can be bound to the R1 and R2 positions through a suitable chemical bond. In some embodiments, the moiety is —H, providing a lysophospholipid with a fatty acid moiety, preferably an omega-3 fatty acid moiety at either the R1 or R2 position. In other embodiments, the organic moiety is a fatty acid moiety bound to the R1 or R2 position via an ester, ether or vinyl ether bond. Exemplary fatty acids moieties include, but are not limited to, omega-3, omega-6 and omega-9 moieties, including, but not limited to, Eicosatrienoic acid (ETE; 20:3 (n-3); all-cis-11,14,17-eicosatrienoic acid); Eicosatetraenoic acid (ETA; 20:4 (n-3); all-cis-8,11,14,17-eicosatetraenoic acid); Eicosapentaenoic acid (EPA; 20:5 (n-3); all-cis-5,8,11,14,17-eicosapentaenoic acid); Heneicosapentaenoic acid (HPA; 21:5 (n-3); all-cis-6,9,12,15,18-heneicosapentaenoic acid); Docosapentaenoic acid (DPA; 22:5 (n-3); all-cis-7,10,13,16,19-docosapentaenoic acid; Docosahexaenoic acid (DHA; 22:6 (n-3); all-cis-4,7,10,13,16,19-docosahexaenoic acid); Tetracosapentaenoic acid (24:5 (n-3); all-cis-9,12,15,18,21-tetracosapentaenoic acid; and Tetracosahexaenoic acid (24:6 (n-3) all-cis-6,9,12,15,18,21-tetracosahexaenoic acid). In some embodiments, the LC-PUFA moiety is preferably an omega-6 fatty acid moiety selected from the group consisting of Eicosadienoic acid (20:2 (n-6); all-cis-11,14-eicosadienoic acid); Dihomo-gamma-linolenic acid (DGLA; 20:3 (n-6) all-cis-8,11,14-eicosatrienoic acid; Arachidonic acid (AA; 20:4 (n-6); all-cis-5,8,11,14-eicosatetraenoic acid); Docosadienoic acid (22:2 (n-6); all-cis-13,16-docosadienoic acid); Adrenic acid (22:4 (n-6) all-cis-7,10,13,16-docosatetraenoic acid; Docosapentaenoic acid (22:5 (n-6); all-cis-4,7,10,13,16-docosapentaenoic acid); Tetracosatetraenoic acid (24:4 (n-6); all-cis-9,12,15,18 tetracosatetraenoic acid); and Tetracosapentaenoic acid (24:5 (n-6); all-cis-6,9,12,15,18-tetracosapentaenoic acid). In some embodiments, the LC-PUFA moiety is preferably an omega-9 fatty acid moiety such as mead acid (20:3 (n-9); 5,8,11-eicosatrienoic acid), as well as decanoic acid (10:0), undecanoic acid (11:0), 10-undecanoic acid (11:1), lauric acid (12:0), cis-5-dodecanoic acid (12:1), tridecanoic acid (13:0), myristic acid (14:0), myristoleic acid (cis-9-tetradecenoic acid, 14:1), pentadecanoic acid (15:0), palmitic acid (16:0), palmitoleic acid (cis-9-hexadecenoic acid, 16:1), heptadecanoic acid (17:1), stearic acid (18:0), elaidic acid (trans-9-octadecenoic acid, 18:1), oleic acid (cis-9-octadecanoic acid, 18:1), nonadecanoic acid (19:0), eicosanoic acid (20:0), cis-11-eicosenoic acid (20:1), 11,14-eicosadienoic acid (20:2), heneicosanoic acid (21:0), docosanoic acid (22:0), erucic acid (cis-13-docosenoic acid, 22:1), tricosanoic acid (23:0), tetracosanoic acid (24:0), nervonic acid (24:1), pentacosanoic acid (25:0), hexacosanoic acid (26:0), heptacosanoic acid (27:0), octacosanoic acid (28:0), nonacosanoic acid (29:0), triacosanoic acid (30:0), vaccenic acid (t-11-octadecenoic acid, 18:1), tariric acid (octadec-6-ynoic acid, 18:1), and ricinoleic acid (12-hydroxyoctadec-cis-9-enoic acid, 18:1). In some embodiments, the fatty acids moieties may be conjugated, hydroxylated, epoxidated or hydroxyepoxidated acyl residues.

In some embodiments, the fatty acid content of the phospholipid composition is from about 1% to about 99% omega-3 fatty acid moieties on a weight/weight basis (w/w; calculated as the weight of omega-3 fatty acid moieties in the phospholipid fraction divided by the total weight of fatty acids in the phospholipid fraction) or molar ratio basis (moles of omega-3 fatty acid moieties in the composition expressed as a percentage of the moles total fatty acids), 10% to 40% omega-3 fatty acid moieties w/w or molar ratio, 20% to 40% omega-3 fatty acid moieties w/w or molar ratio, 20% to 50% omega-3 fatty acid moieties w/w or molar ratio, 40% to 60% omega-3 fatty acid moieties w/w or molar ratio, 40% to 99% omega-3 fatty acid moieties w/w or molar ratio, 60% to 99% omega-3 fatty acid moieties w/w or molar ratio, or 80% to 99% LC-PUFA w/w or molar ratio. The w/w % may preferably be determined by an analytical method selected from the group consisting of gas chromatography (GC), high performance liquid chromatography (HPLC), GC-mass spectrometry (GC-MS), nuclear magnetic resonance (NMR) or other suitable methods as is known in the art. In some preferred embodiments, the omega-3 fatty acid moieties are preferably selected from DHA, EPA and combinations thereof. In some embodiments, more than 90% w/w of the omega-3 fatty acid moieties, preferably more than 95% w/w of the omega-3 fatty acid moieties, and most preferably more than about 98% w/w of the omega-3 fatty acid moieties are distributed at the R2 position. In some preferred embodiments, the omega-3 fatty acid moieties are greater than 50%, 60%, 70%, 80%, 90% or 95% w/w EPA and/or DHA. In some embodiments, the ratio of EPA to DPA is from about 10:1 to 1:10, 3:1 to 1:3, 5:1 to 1:1, 3:1 to 1:1, 2:1 to 1:1, 1:1 to 1:3, or 1:1 to 1:5 on a molar basis. In some embodiments, the compositions comprise greater than about 40%, 50%, 60%, 70%, 80%, 90% or 95% phospholipid compounds w/w.

The phospholipid compounds of the present invention may be provided from a variety of sources. In some embodiments, the phospholipids are from a natural source, for example krill, herring, herring roe, copepods or other suitable sources. A suitable krill oil is described in WO/2008/117602, the entire contents of which are incorporated herein by reference. A suitable phospholipid concentrate produced from krill oil is described in WO/2008/060163 and WO/2009/139641, the entire contents of each of which are incorporated herein by reference.

In some embodiments, the present invention utilizes a krill oil composition, preferably a *Euphausia superba* krill oil composition, comprising from about 40% to about 60% w/w phospholipids, preferably from about 45% to 55% w/w phospholipids and from about 100 mg/kg astaxanthin to about 2500 mg/kg astaxanthin. In some preferred embodiments, the compositions of the present invention comprise from about 1%, 2%, 3% or 4% to about 8%, 10%, 12% or 15% w/w ether phospholipids or greater than about 4%, 5%, 6%, 7%, 8%, 9% or 10% ether phospholipids. In some embodiments the ether phospholipids are preferably alkylacylphosphatidylcholine, lyso-alkylacylphosphatidylcholine, alkylacylphosphatidylethanolamine or combinations thereof. In some embodiments, the compositions comprise from about 1%, 2%, 3% or 4% to about 8%, 10%, 12% or 15% w/w ether phospholipids and from about 30%, 33%, 40%, 42%, 45%, 48%, 50%, 52%, 54%, 55% 56%, 58% to about 60% non-ether phospholipids so that the total amount of phospholipids (both ether and non-ether phospholipids) ranges from about 40% to about 60%. One of skill in the art will recognize that the range of 40% to 60% total phospholipids, as well as the other ranges of ether and non-ether phospholipids, can include other values not specifically listed within the range. In other embodiments, the phospholipid compounds may be produced by synthetic processes. Suitable synthetic processes are described, for example, in WO/2006/054183, the entire content of which are incorporated herein by reference.

In some embodiments, the phospholipid compositions described above preferably comprise one or more additional omega-3 fatty acid derivatives or free fatty acids. In some embodiments, the one or more additional omega-3 fatty acid derivatives are selected from omega-3 esters and glycerides. For example, in some embodiments, the composition may comprise from about 1% to about 60% phospholipids, with the remaining 99% to 40% of the composition being omega-3 glycerides, esters, or free fatty acids or a combination thereof. In some embodiments, the composition may comprise from about 5% to about 60% phospholipids, with the remaining 95% to 40% of the composition being omega-3 glycerides, esters, or free fatty acids or a combination thereof. In some embodiments, the composition may comprise from about 20% to about 60% phospholipids, with the remaining 80% to 40% of the composition being omega-3 glycerides, esters, or free fatty acids or a combination thereof. In some embodiments, the composition may comprise from about 30% to about 60% phospholipids, with the remaining 70% to 40% of the composition being omega-3 glycerides, esters, or free fatty acids or a combination thereof. In some embodiments, the composition may comprise from about 40% to about 60% phospholipids, with the remaining 60% to 40% of the composition being omega-3 glycerides, esters, or free fatty acids or a combination thereof. In some embodiments, the composition may comprise from about 50% to about 60% phospholipids, with the remaining 50% to 40% of the composition being omega-3 glycerides, esters, or free fatty acids or a combination thereof.

In some embodiments, the LC-PUFA derivative is an ester. Suitable esters include, but are not limited to, ethyl esters and methyl esters of LC-PUFAs. In some embodiments, the ester composition approximates that of Lovaza® (i.e., 1 gram of the ester composition contains approximately 465 mg EPA ethyl ester, approximately 375 mg DHA ethyl ester, and approximately 80 mg of other omega-3 fatty acids. Preferred fatty acid moieties are listed above in the description for phospholipid compounds. Particularly preferred omega-3 fatty acid esters include esters of EPA, DHA, and combination thereof. In some embodiments, the compositions comprise an ester fraction comprising a mixture of two or more of the esters described above. In some embodiments, the fatty acid content of the ester fraction is from about 1% to about 99% omega-3 fatty acid moieties on a weight/weight basis (w/w; calculated as the weight of LC-PUFA in the ester fraction divided by the total weight of fatty acids in the ester fraction) or molar ratio basis (moles of omega-3 fatty acid moieties in the composition expressed as a percentage of the moles total fatty acids), 10% to 40% omega-3 fatty acid moieties w/w or molar ratio, 20% to 40% omega-3 fatty acid moieties w/w or molar ratio, 20% to 50% omega-3 fatty acid moieties w/w or molar ratio, 40% to 60% omega-3 fatty acid moieties w/w or molar ratio, 40% to 99% omega-3 fatty acid moieties w/w or molar ratio, 60% to 99% omega-3 fatty acid moieties w/w or molar ratio, or 80% to 99% LC-PUFA w/w or molar ratio. The w/w % may preferably be determined by an analytical method selected from the group consisting of gas chromatography (GC), high performance liquid chromatography (HPLC), GC-mass spectrometry (GC-MS), nuclear magnetic resonance (NMR) or other suitable methods as is known in the art. In some preferred embodiments, the omega-3 fatty acid moieties in the esters are greater than 50%, 60%, 70%, 80%, 90% or 95% w/w EPA and/or DHA. In some embodiments, the ratio of EPA to DPA is from about 10:1 to 1:10, 3:1 to 1:3, 5:1 to 1:1, 3:1 to 1:1, 2:1 to 1:1, 1:1 to 1:3, or 1:1 to 1:5 on a molar basis. In some embodiments, the compositions comprise greater than about 5%, 10%, 20%, 30%, 40%, 50%, 60%, 70%, 80%, 90% or 95% omega-3 esters w/w, with the remainder of the composition being at least one of an omega-3 phospholipid composition as described above, an omega-3 glyceride composition as described below, or an omega-3 fatty acid composition as described below.

The ester compounds and compositions of the present invention may be provided from a variety of sources. In some embodiments, the esters compositions are prepared from a marine oil starting material. Suitable marine oils include, but are not limited to, krill oil, tuna oil, herring oil, menhaden oil, cod liver oil and algae oil. Methods for increasing the concentration of desirable omega-3 fatty acid moieties such as EPA and DHA in the esters are known in the art. See, e.g., WO/2009/139641, WO/2008/060163, and U.S. Pat. No. 5,656,667, the entire contents of each of which are incorporated herein by reference.

In some embodiments, the omega-3 derivative is a composition comprising glyceride compounds. Suitable glyceride compounds include, but are not limited to, those described by the following structure:

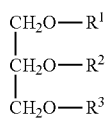

wherein R1, R2, and R3 are a fatty acid moiety or H. Preferred fatty acid moieties are described above in the description of the phospholipid and ester compounds and compositions. In some embodiments, the fatty acid content of the glyceride composition is from about 1% to about 99% omega-3 fatty acid moieties on a weight/weight basis (w/w; calculated as the weight of omega-3 fatty acid moieties in the glyceride fraction divided by the total weight of fatty acids in the glyceride fraction) or molar ratio basis (moles of omega-3 fatty acid moieties in the composition expressed as a percentage of the moles total fatty acids), 10% to 40% omega-3 fatty acid moieties w/w or molar ratio, 20% to 40% omega-3 fatty acid moieties w/w or molar ratio, 20% to 50% omega-3 fatty acid moieties w/w or molar ratio, 40% to 60% omega-3 fatty acid moieties w/w or molar ratio, 40% to 99% omega-3 fatty acid moieties w/w or molar ratio, 60% to 99% omega-3 fatty acid moieties w/w or molar ratio, or 80% to 99% LC-PUFA w/w or molar ratio. The w/w % may preferably be determined by an analytical method selected from the group consisting of gas chromatography (GC), high performance liquid chromatography (HPLC), GC-mass spectrometry (GC-MS), nuclear magnetic resonance (NMR) or other suitable methods as is known in the art. In some preferred embodiments, the omega-3 fatty acid moieties are preferably selected from DHA, EPA and combinations thereof. In some preferred embodiments, the omega-3 fatty acid moieties are greater than 50%, 60%, 70%, 80%, 90% or 95% w/w EPA and/or DHA. In some embodiments, the ratio of EPA to DPA is from about 10:1 to 1:10, 3:1 to 1:3, 5:1 to 1:1, 3:1 to 1:1, 2:1 to 1:1, 1:1 to 1:3, or 1:1 to 1:5 on a molar basis. In some embodiments, the compositions comprise greater than about 40%, 50%, 60%, 70%, 80%, 90% or 95% glycerides w/w, with the remainder of the composition being at least one of an omega-3 phospholipid composition as described above, an omega-3 ester composition as described above, or an omega-3 fatty acid composition as described below.

The glyceride compounds and compositions of the present invention may be provided from a variety of sources. In some embodiments, the glyceride compositions provided as a marine oil. Suitable marine oils include, but are not limited to, krill oil, tuna oil, herring oil, menhaden oil, cod liver oil and algae oil. A suitable krill oil is described in WO/2008/117602, the entire contents of which are incorporated herein by reference. The glycerides may also be produced synthetically. For example, it is known in the art that fish oils with concentrated amounts of desired LC-PUFA moieties such as EPA and DHA may be produced by transesterification or hydrolysis of a marine oil starting materials in order to give esters (typically ethyl esters) or free fatty acids or other derivatives that are suitable for further concentration of the omega-3 fatty acids. In some embodiments, the omega-3 esters are reesterified to a glyceride molecule to provide an oil with an increased concentration of omega-3 fatty acids. See, e.g., WO/2009/139641 and WO/2008/060163, the entire contents of which are incorporated herein by reference.

In some embodiments, the composition further comprise omega-3 free fatty acids. Preferred omega-3 free fatty acids are listed above in the description for phospholipid compounds. Particularly preferred omega-3 free fatty acids include EPA, DHA, and combination thereof. In some embodiments, compositions comprising the free fatty acids are utilized. In some embodiments, the compositions comprise a free fatty acid fraction comprising a mixture of two or more of the free fatty acids described above. In some embodiments, the fatty acid content of the composition is from about 1% to about 99% omega-3 free fatty acids on a weight/weight basis (w/w; calculated as the weight of omega-3 free fatty acids in the composition divided by the total weight of fatty acids in the composition) or molar ratio basis (moles of omega-3 fatty acid moieties in the composition expressed as a percentage of the moles total fatty acids), 10% to 40% omega-3 fatty acid moieties w/w or molar ratio, 20% to 40% omega-3 fatty acid moieties w/w or molar ratio, 20% to 50% omega-3 fatty acid moieties w/w or molar ratio, 40% to 60% omega-3 fatty acid moieties w/w or molar ratio, 40% to 99% omega-3 fatty acid moieties w/w or molar ratio, 60% to 99% omega-3 fatty acid moieties w/w or molar ratio, or 80% to 99% LC-PUFA w/w or molar ratio. The w/w % may preferably be determined by an analytical method selected from the group consisting of gas chromatography (GC), high performance liquid chromatography (HPLC), GC-mass spectrometry (GC-MS), nuclear magnetic resonance (NMR) or other suitable methods as is known in the art. In some preferred embodiments, the omega-3 free fatty acids content in the composition greater than 50%, 60%, 70%, 80%, 90% or 95% w/w EPA and/or DHA. In some embodiments, the ratio of EPA to DPA is from about 10:1 to 1:10, 3:1 to 1:3, 5:1 to 1:1, 3:1 to 1:1, 2:1 to 1:1, 1:1 to 1:3, or 1:1 to 1:5 on a molar basis. In some embodiments, the compositions comprise greater than about 40%, 50%, 60%, 70%, 80%, 90% or 95% omega-3 free fatty acid w/w, with the remainder of the composition being at least one of an omega-3 phospholipid composition as described above, an omega-3 ester composition as described above, or an omega-3 glyceride composition as described above.

The free fatty acids and free fatty acid compositions of the present invention may be provided from a variety of sources. In some embodiments, the compositions are prepared from a marine oil starting material. Suitable marine oils include, but are not limited to, krill oil, tuna oil, herring oil, menhaden oil, cod liver oil and algae oil. Methods for increasing the concentration of desirable omega-3 fatty free fatty acids such as EPA and DHA are known in the art. See, e.g., WO/2009/139641, WO/2008/060163, and U.S. Pat. No. 5,656,667, the entire contents of each of which are incorporated herein by reference.

In some embodiments, the compounds or compositions described above are administered to a subject in need thereof to treat a disease or condition associated with red blood cells and cell membranes, and in particular a disease or conditions associated with an abnormality in red blood cells of cell membranes. In some embodiments, the condition or disease is sickle cell disease, sickle cell anemia, or sickle cell trait. In some embodiments, the condition or disease is thalassemia (alpha-, beta- or delta-), thalassemia in combination with a hemoglobinopathy (Hemoglobin E, Hemoglobin S, or Hemoglobin C), splenomegaly, or membrane abnormities such as acanthocytes or spur/spike cells, codocytes (target cells), echinocytes (burr cells), elliptocytes and ovalocytes, spherocytes, stomatocytes (mouth cells) and degmacytes ("bite cells").

In some embodiments, an effective amount of the compounds or compositions described above are administered to a subject in need thereof to treat or prevent a cardiometabolic disorder/metabolic syndrome. In some embodiments, the cardiometabolic disorder is selected from atherosclerosis, arteriosclerosis, coronary heart (carotid artery) disease (CHD or CAD), acute coronary syndrome (or ACS), valvular heart disease, aortic and mitral valve disorders, arrhythmia/atrial fibrillation, cardiomyopathy and heart failure, angina pectoris, acute myocardial infarction (or AMI), hypertension, orthostatic hypotension, shock, embolism (pulmonary and venous), endocarditis, diseases of arteries, the aorta and its branches, disorders of the peripheral vascular system (peripheral arterial disease or PAD), Kawasaki disease, congenital heart disease (cardiovascular defects) and stroke (cerebrovascular disease), dyslipidemia, hypertriglyceridemia, hypertension, heart failure, cardiac arrhythmias, low HDL levels, high LDL levels, stable angina, coronary heart disease, acute myocardial infarction, secondary prevention of myocardial infarction, cardiomyopathy, endocarditis, type 2 diabetes, insulin resistance, impaired glucose tolerance, hypercholesterolemia, stroke, hyperlipidemia, hyperlipoproteinemia, chronic kidney disease, intermittent claudication, hyperphosphatemia, omega-3 deficiency, phospholipid deficiency, carotid atherosclerosis, peripheral arterial disease, diabetic nephropathy, hypercholesterolemia in HIV infection, acute coronary syndrome (ACS), non-alcoholic fatty liver disease/non-alcoholic steatohepatitis (NAFLD/NASH), arterial occlusive diseases, cerebral atherosclerosis, arteriosclerosis, cerebrovascular disorders, myocardial ischemia, coagulopathies leading to thrombus formation in a vessel and diabetic autonomic neuropathy.

In some embodiments, an effective amount of the compounds or compositions described above are administered to a subject in need thereof to treat, prevent, or improve cognition and/or a cognitive disease, disorder or impairment (memory, concentration, learning (deficit)), or to treat or prevent neurodegenerative disorders. In some embodiments, the cognitive disease, disorder or impairment is selected from Attention Deficit Disorder (ADD), Attention Deficit Hyperactivity Disorder (ADHD), autism/autism spectrum disorder (ASD), (dyslexia, age-associated memory impairment and learning disorders, amnesia, mild cognitive impairment, cognitively impaired non-demented, pre-Alzheimer's disease, Alzheimer's disease, epilepsy, Pick's disease, Huntington's disease, Parkinson disease, Lou Gehrig's disease, pre-dementia syndrome, Lewy body dementia dementia, dentatorubropallidoluysian atrophy, Freidreich's ataxia, multiple system atrophy, types 1, 2, 3, 6, 7 spinocerebellar ataxia, amyotrophic lateral sclerosis, familial spastic paraparesis, spinal muscular atrophy, spinal and bulbar muscular atrophy, age-related cognitive decline, cognitive deterioration, moderate mental impairment, mental deterioration as a result of ageing, conditions that influence the intensity of brain waves and/or brain glucose utilization, stress, anxiety, concentration and attention impairment, mood deterioration, general cognitive and mental well being, neurodevelopmental, neurodegenerative disorders, hormonal disorders, neurological imbalance or any combinations thereof. In a specific embodiment, the cognitive disorder is memory impairment.

In some embodiments, an effective amount of the compounds or compositions described above are administered to a subject in need thereof to inhibit, prevent, or treat inflammation or an inflammatory disease. In some embodiments, the inflammation or inflammatory disease is selected from organ transplant rejection; reoxygenation injury resulting from organ transplantation (see Grupp et al., J. Mol. Cell. Cardiol. 31: 297-303 (1999)) including, but not limited to, transplantation of the following organs: heart, lung, liver and kidney; chronic inflammatory diseases of the joints, including arthritis, rheumatoid arthritis, osteoarthritis and bone diseases associated with increased bone resorption; inflammatory bowel diseases (IBD) such as ileitis, ulcerative colitis (UC), Barrett's syndrome, and Crohn's disease (CD); inflammatory lung diseases such as asthma, acute respiratory distress syndrome (ARDS), and chronic obstructive pulmonary disease (COPD); inflammatory diseases of the eye including corneal dystrophy, trachoma, onchocerciasis, uveitis, sympathetic ophthalmitis and endophthalmitis; chronic inflammatory diseases of the gum, including gingivitis and periodontitis; inflammatory diseases of the kidney including uremic complications, glomerulonephritis and nephrosis; inflammatory diseases of the skin including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, Epilepsy, amyotrophic lateral sclerosis and viral or autoimmune encephalitis, preeclampsia; chronic liver failure, brain and spinal cord trauma, and cancer. The inflammatory disease can also be a systemic inflammation of the body, exemplified by gram-positive or gram negative shock, hemorrhagic or anaphylactic shock, or shock induced by cancer chemotherapy in response to proinflammatory cytokines, e.g., shock associated with proinflammatory cytokines. Such shock can be induced, e.g., by a chemotherapeutic agent that is administered as a treatment for cancer. Other disorders include depression, obesity, allergic diseases, acute cardiovascular events, muscle wasting diseases, and cancer cachexia. Also inflammation that results from surgery and trauma can be treated with the concentrated therapeutic phospholipid compositions.

In some embodiments, the effective amount comprises from about 0.1 to about 5 grams of the omega-3 compound or composition, preferably from about 0.2 to about 3 grams of the omega-3 compound or composition, and most preferably about 0.5 to about 1.5 grams of the omega-3 compound or composition.

The LC-PUFA compounds and compositions of the present invention may be used to treat a variety of subjects. Suitable subjects include humans as well as domestic animals, non-human primates, and companion animals such as dogs, cats and birds.

The compounds and compositions of the present invention are preferably administered intravenously or orally. Accordingly, in some embodiments, the compositions of this invention (such as those described in the preceding sections) are contained in acceptable excipients and/or carriers for oral consumption or for intravenous administration. The actual form of the carrier, and thus, the composition itself, is not critical. The carrier may be a liquid, gel, gelcap, capsule, powder, solid tablet (coated or non-coated), tea, or the like. The composition is preferably in the form of a tablet or capsule and most preferably in the form of a soft gel capsule. Suitable excipient and/or carriers include vegetable oil, fish oil, krill oil, maltodextrin, calcium carbonate, dicalcium phosphate, tricalcium phosphate, microcrystalline cellulose, dextrose, rice flour, magnesium stearate, stearic acid, croscarmellose sodium, sodium starch glycolate, crospovidone, sucrose, vegetable gums, lactose, methylcellulose, povidone, carboxymethylcellulose, corn starch, and the like (including mixtures thereof). Preferred carriers include calcium carbonate, magnesium stearate, maltodextrin, and mixtures thereof. The various ingredients and the excipient and/or carrier are mixed and formed into the desired form using conventional techniques. The tablet or capsule of the present invention may be coated with an enteric coating that dissolves at a pH of about 6.0 to 7.0. A suitable enteric coating that dissolves in the small intestine but not in the stomach is cellulose acetate phthalate. Further details on techniques for formulation for and administration may be found in the latest edition of Remington's Pharmaceutical Sciences (Maack Publishing Co., Easton, Pa.). For intravenous or oral administration, the omega-3 compounds and compositions of the present invention may preferably be provided as emulsions.

In some embodiments, the compounds and compositions are formulated for oral administration with flavoring agents or sweeteners. Examples of useful flavoring include, but are not limited to, pure anise extract, imitation banana extract, imitation cherry extract, chocolate extract, pure lemon extract, pure orange extract, pure peppermint extract, imitation pineapple extract, imitation rum extract, imitation strawberry extract, or pure vanilla extract; or volatile oils, such as balm oil, bay oil, bergamot oil, cedarwood oil, walnut oil, cherry oil, cinnamon oil, clove oil, or peppermint oil; peanut butter, chocolate flavoring, vanilla cookie crumb, butterscotch or toffee. In one embodiment, the dietary supplement contains cocoa or chocolate.

Emulsifiers may be added for stability of the final product. Examples of suitable emulsifiers include, but are not limited to, lecithin (e.g., from egg or soy), and/or mono- and di-glycerides. Other emulsifiers are readily apparent to the skilled artisan and selection of suitable emulsifier(s) will depend, in part, upon the formulation and final product. In addition to the carbohydrates described above, the nutritional supplement can contain natural or artificial (preferably low calorie) sweeteners, e.g., saccharides, cyclamates, aspartamine, aspartame, acesulfame K, and/or sorbitol.

The compositions of the present invention may also be delivered as dietary supplements, nutritional supplements, or functional foods.

The dietary supplement may comprise one or more inert ingredients, especially if it is desirable to limit the number of calories added to the diet by the dietary supplement. For example, the dietary supplement of the present invention may also contain optional ingredients including, for example, herbs, vitamins, minerals, enhancers, colorants, sweeteners, flavorants, inert ingredients, and the like. For example, the dietary supplement of the present invention may contain one or more of the following: asorbates (ascorbic acid, mineral ascorbate salts, rose hips, acerola, and the like), dehydroepiandosterone (DHEA), green tea (polyphenols), inositol, kelp, dulse, bioflavinoids, maltodextrin, nettles, niacin, niacinamide, rosemary, selenium, silica (silicon dioxide, silica gel, horsetail, shavegrass, and the like), spirulina, zinc, and the like. Such optional ingredients may be either naturally occurring or concentrated forms.

In some embodiments, the dietary supplements further comprise vitamins and minerals including, but not limited to, calcium phosphate or acetate, tribasic; potassium phosphate, dibasic; magnesium sulfate or oxide; salt (sodium chloride); potassium chloride or acetate; ascorbic acid; ferric orthophosphate; niacinamide; zinc sulfate or oxide; calcium pantothenate; copper gluconate; riboflavin; beta-carotene; pyridoxine hydrochloride; thiamin mononitrate; folic acid; biotin; chromium chloride or picolonate; potassium iodide; sodium selenate; sodium molybdate; phylloquinone; vitamin $D_3$; cyanocobalamin; sodium selenite; copper sulfate; vitamin A; vitamin C; inositol; potassium iodide. Suitable dosages for vitamins and minerals may be obtained, for example, by consulting the U.S. RDA guidelines.

In other embodiments, the present invention provides nutritional supplements (e.g., energy bars or meal replacement bars or beverages) comprising of the compositions of the present invention. In preferred embodiments, the nutritional supplements comprise an effective amount of the components as described above. The nutritional supplement may serve as meal or snack replacement and generally provide nutrient calories. Preferably, the nutritional supplements provide carbohydrates, proteins, and fats in balanced amounts. The nutritional supplement can further comprise carbohydrate, simple, medium chain length, or polysaccharides, or a combination thereof. A simple sugar can be chosen for desirable organoleptic properties. Uncooked cornstarch is one example of a complex carbohydrate. If it is desired that it should maintain its high molecular weight structure, it should be included only in food formulations or portions thereof which are not cooked or heat processed since the heat will break down the complex carbohydrate into simple carbohydrates, wherein simple carbohydrates are mono- or disaccharides. The nutritional supplement contains, in one embodiment, combinations of sources of carbohydrate of three levels of chain length (simple, medium and complex; e.g., sucrose, maltodextrins, and uncooked cornstarch).

In still further embodiments, the present invention provides food products, prepared food products, or foodstuffs (i.e., functional foods) comprising of the fatty acids or derivatives thereof. In preferred embodiments, the foods comprise an effective amount of the components as described above. For example, in some embodiments, beverages and solid or semi-solid foods comprising the fatty acids or derivatives thereof are provided. These forms can include, but are not limited to, beverages (e.g., soft drinks, milk and other dairy drinks, and diet drinks), baked goods, puddings, dairy products, confections, snack foods, or frozen confections or novelties (e.g., ice cream, milk shakes), prepared frozen meals, candy, snack products (e.g., chips), soups, spreads, sauces, salad dressings, prepared meat products, cheese, yogurt and any other fat or oil containing foods, and food ingredients (e.g., wheat flour).

All publications and patents mentioned in the above specification are herein incorporated by reference. Various modifications and variations of the described compounds, compositions, methods and uses of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the medical, biological and chemical sciences are intended to be within the scope of the following claims.

EXAMPLES

Example 1

One part krill oil, one part fish oil triglycerides and one part omega-3 ethyl ester concentrate (e.g., Lovaza) are mixed together and filled into a gel capsule.

Example 2

One part krill oil, one part fish oil triglycerides and two parts omega-3 ethyl ester concentrate (e.g., Lovaza) are mixed together and filled into a gel capsule.

Example 3

One part krill oil and two parts omega-3 ethyl ester concentrate (e.g., Lovaza) are mixed together and filled into a gel capsule.

Example 4

One part krill oil and four parts omega-3 ethyl ester concentrate (e.g., Lovaza) are mixed together and filled into a gel capsule.

Example 5

One part krill oil and two parts fish oil triglycerides are mixed together and filled into a gel capsule.

Example 6

One part krill oil and four parts fish oil triglycerides are mixed together and filled into a gel capsule.

Example 7

Five parts krill oil and one part omega-3 ethyl ester concentrate (e.g., Lovaza) are mixed together and filled into a gel capsule.

Example 8

One part krill oil and ten parts omega-3 ethyl ester concentrate (e.g., Lovaza) are mixed together and filled into a gel capsule.

The invention claimed is:

1. A composition comprising a krill oil fraction having a phospholipid content of from 40% to 50% phospholipids w/w and a fatty acid ethyl ester fraction, wherein said composition is characterized in comprising at least 50% w/w of said fatty acid ethyl ester fraction and wherein said fatty acid ethyl ester fraction comprises fish oil ethyl esters having a eicosapentaenoic acid and docosahexaenoic acid content of greater than 50% w/w.

2. The composition of claim 1, wherein said composition comprises at least 5% w/w of said phospholipid compounds.

3. The composition of claim 1, wherein said composition comprises at least 25% w/w of said phospholipid compounds.

4. The composition of claim 1, wherein said composition comprises astaxanthin.

5. The composition of claim 4, wherein said composition comprises an antioxidant in addition to said astaxanthin.

6. The composition of claim 1, wherein said composition is provided in a formulation selected from the group consisting of a capsule, a liquid, an emulsion, a dietary supplement, a nutritional supplement, a beverage and a functional food.

* * * * *